(12) United States Patent
Nam

(10) Patent No.: US 7,862,839 B2
(45) Date of Patent: Jan. 4, 2011

(54) FUNCTIONAL FOOD COMPOSITION FOR TREATING ALLERGY, NATURAL TEA USING THE SAME AND THE MANUFACTURING METHOD THEREOF

(76) Inventor: Jong Hyun Nam, 21-8, Geoyeo-dong, Songpa-gu, Seoul (KR)

( * ) Notice: Subject to any disclaimer, the term of this patent is extended or adjusted under 35 U.S.C. 154(b) by 233 days.

(21) Appl. No.: 12/094,797

(22) PCT Filed: Nov. 27, 2007

(86) PCT No.: PCT/KR2007/006017

§ 371 (c)(1),
(2), (4) Date: May 23, 2008

(87) PCT Pub. No.: WO2008/069484

PCT Pub. Date: Jun. 12, 2008

(65) Prior Publication Data

US 2008/0311229 A1    Dec. 18, 2008

(30) Foreign Application Priority Data

Dec. 5, 2006    (KR) .................... 10-2006-0122386

(51) Int. Cl.
*A61K 36/68* (2006.01)
*A61K 36/00* (2006.01)

(52) U.S. Cl. ........................ 424/738; 424/725

(58) Field of Classification Search .............. None
See application file for complete search history.

(56) References Cited

U.S. PATENT DOCUMENTS

| 6,811,796 B2 * | 11/2004 | Yoshida ............... 424/738 |
| 2004/0071796 A1 * | 4/2004 | Li ....................... 424/735 |

FOREIGN PATENT DOCUMENTS

| JP | 360105623 | * | 6/1985 |
| KR | 2002059320 | * | 7/2002 |
| KR | 2003026942 | * | 4/2003 |
| KR | 2003083160 | * | 10/2003 |
| KR | 1020040030371 A | | 4/2004 |
| KR | 2005101942 | * | 10/2005 |
| KR | 1020050101942 A | | 10/2005 |
| KR | 2006111790 | * | 10/2006 |
| KR | 2009051874 | * | 5/2009 |

OTHER PUBLICATIONS

Lee et al. Am. J. Chinese Med. 1997. vol. 25, No. 1, pp. 51-56, BIOSIS Abstract enclosed.*
Bong-Keun Song et al., The Study on the Antiallergic Action of *Poncirus triofoliata*, Korean J. Orient. Int. Med., 2000, 156-161, V.21, No. 1.
Suk Min Hee et al., Inhibitory Effect of *Saururus chinensis* (Lour.) Bail! Extracts on Allergy in Mouse Models, Korean J. Orient. Phys. & Path., 2005, 146-151, V.19, No. 1.
Eun-Mi Choi et al., Inhibitory Effect on Delayed-Type Hypersensitivity by the Hot Water Extracts from Medicinal Herbs, Korean J. Food Sci. Tech., 2001, 146-148, V.33, No. 1.
Yong-Dea Aeom et al., The Comparative Study of Fructus Immaturus Ponciri and *Fructus ponciri* Effect on Allergic Reaction, J. Korean Orient. Med., 2001, 156-161, V.21, No. 1.
Kim, Hyeong-Kyun et al, "The Study on the Antiallergic Action of *Poncirus trifoliata*", Journal of Korean Oriental Internal Medicine, Aug. 30, 2000, 156-161, 21, 1.
Yongdae Aeom et al, "The Comparative Study of Fructus Immaturus Ponciri and *Fructus ponciri* . . . " Journal of Korean Oriental Medicine, Dec. 29, 2001, 10-21, 22, 4.
Suk, Min-Hee et al, "Inhibitory Effect of *Saururus chinensis* (Lour.) Belli Extracts . . . " Journal of Oriental Medical Physiology, Feb. 25, 2005, 146-151, 19, 1.
Choi, Eun-Mi et al, "Inhibitory Effect on Delayed-type Hypersensivity . . . ", Korean Journal of Food Science and Technology, Feb. 28, 2001, 146-148, 33, 1.

* cited by examiner

*Primary Examiner*—Christopher R. Tate
(74) *Attorney, Agent, or Firm*—IpHorgan Ltd.

(57) ABSTRACT

A functional food composition for treating allergy, comprising *Saururus chinensis*, *Plantago asiatica*, *Poncirus trifoliata* and *Schisandra chinensis* extracts, as active ingredients, a tea composition comprising the same and a manufacturing method thereof. The functional food and tea compositions for treatment of allergy in accordance with the present invention are therapeutically effective for any type of allergic diseases, irrespective of allergic causes. In particular, the tea composition advantageously enables easy and regular administration at need, which can achieve anti-allergic effects without particular efforts for treatment of diseases.

8 Claims, No Drawings

FUNCTIONAL FOOD COMPOSITION FOR TREATING ALLERGY, NATURAL TEA USING THE SAME AND THE MANUFACTURING METHOD THEREOF

BACKGROUND OF THE INVENTION

1. Technical Field

The present invention relates to a functional food composition for treating allergy, comprising *Poncirus trifoliata* extract, and *Saururus chinensis* extract, *Schisandra chinensis* extract or *Plantago asiatica* extract, as active ingredients, a tea composition comprising the same and a manufacturing method thereof.

2. Background Art

Allergic diseases have become serious problems with the advance of civilization, particularly in advanced industrial countries. In the United States, American people are currently afflicted with more than 20 kinds of allergic diseases, predominantly dermatitis, asthma and rhinitis. Further, the incidence of allergic patients in Korea is comparable to the level of advanced countries and has been increasing year by year.

Generally, manifestation of allergy in the body is accompanied by atopic dermatitis, urticaria, bronchial asthma, allergic rhinitis, allergic keratitis, and the like. Mast cells are primarily implicated in the manifestation of allergy. Histamine, a primary allergic mediator released from mast cells, promotes vascular permeability and induces infiltration of inflammatory cells into target tissues. For that reason, various chemical drugs, such as anti-histamine drugs, antibiotics, and hormone drugs, have been largely used for treatment of allergic diseases. However, administration of such therapeutic drugs suffers from adverse side effects such as maldigestion, dizziness, and stomach problems (such as heartburn, upset stomach, and stomach pain), which may occur due to toxicity of the drugs. Further, allergic diseases may become chronic due to the development of resistance to allergens upon chronic administration of the therapeutic agents.

In order to cope with such problems as mentioned above, anti-allergic drugs based on herbal ingredients have been developed. However, such herbal medicines suffer from inconvenience and discomfort associated with postprandial administration of drugs, insignificant therapeutic effects, and administration of drugs which should be made under consideration of physical constitution and symptoms of individual patients.

As a result of a variety of extensive and intensive studies and experiments to solve the problems as described above, the inventors of the present invention have developed a drug which is therapeutically effective for any type of allergic diseases, irrespective of pathogenic causes and patient's predisposition, and which is also capable of providing easy and ordinary administration in conjunction with long-term therapeutic effects. The present invention has been completed based on the development of such an anti-allergic drug.

SUMMARY OF THE INVENTION

Therefore, the present invention has been made in view of the above problems, and it is an object of the present invention to provide a functional food composition for treatment of allergy, which is therapeutically effective for any type of allergic diseases while providing easy administration, via alleviation of pathogenic causes and improvement of patient's constitutional nature and predisposition, a tea composition comprising the same and a method for producing the same.

In accordance with an aspect of the present invention, the above and other objects can be accomplished by the provision of a functional food composition for treatment of allergy, comprising *Poncirus trifoliata* extract as an active ingredient.

The composition of the present invention may further comprise at least one ingredient selected from the group consisting of *Saururus chinensis* extract, *Schisandra chinensis* extract, *Plantago asiatica* extract and any combination thereof, in addition to the *Poncirus trifoliata* extract.

In one embodiment of the present invention, the composition may preferably comprise 20 to 80% by weight of *Poncirus trifoliata* extract, based on the total weight of the herbal extract composition. If a content of the *Poncirus trifoliata* extract is less than 20% by weight, it is difficult to exert anti-allergic effects. However, a content of more than 80% by weight also provides no further increased effects.

In another embodiment of the present invention, the composition may comprise 30 to 80% by weight of *Poncirus trifoliata* extract, 5 to 20% by weight of *Saururus chinensis* extract, 5 to 25% by weight of *Schisandra chinensis* extract, and 5 to 30% by weight of *Plantago asiatica* extract.

The extracts of *Poncirus trifoliata, Saururus chinensis, Schisandra chinensis*, and *Plantago asiatica* herbal plants can be respectively prepared by selecting, washing and chopping a raw material of each herbal medicinal plant, and placing the chopped herbal raw material in a 50 to 60-fold weight of purified water or an aqueous alcoholic solution, followed by extraction at a temperature of 50 to 150° C. for 1 to 10 hours.

If an extraction temperature is less than 50° C., undesirably it is difficult to easily extract active ingredients. On the other hand, if an extraction temperature is higher than 150° C., this may undesirably lead to no improvement in extraction effects and degeneration of active ingredients. Most preferably, an extraction process is carried out at a temperature of 50 to 90° C.

Alcohol is preferably an alcohol of 30 to 70% and includes a lower alcohol such as methanol and ethanol.

Hot water extract or alcoholic extract of the herbal raw material is concentrated at a temperature of 50 to 150° C. for 10 to 24 hours. The resulting concentrate as a main ingredient is mixed with a conventional excipient to prepare a desired composition in accordance with the present invention.

Further, the herbal plant extract in accordance with the present invention may be used as a powder which is obtained by freeze-drying (lyophilization) of the aforementioned extract concentrate at a temperature of −10 to −40° C. for 3 to 20 hours.

In accordance with another aspect of the present invention, there is provided a tea composition for treatment of allergy, comprising 30 to 80% by weight of *Poncirus trifoliata* extract, 5 to 20% by weight of *Saururus chinensis* extract, 5 to 25% by weight of *Schisandra chinensis* extract, and 5 to 30% by weight of *Plantago asiatica* extract, as active ingredients.

In one embodiment of the present invention, a functional tea composition which is therapeutically and/or prophylactically effective for allergic diseases may preferably comprise 10 to 20% by weight of herbal plant extract and 80 to 90% by weight of purified water. If a content of the herbal plant extract is lower than 10% by weight, therapeutic and prophylactic effects are insignificant. On the other hand, if a content of the herbal plant extract is higher than 20% by weight, the individual may suffer from difficulties associated with oral administration of the composition.

The tea composition may further comprise additives which are commonly added to drink or beverage preparations, such as sweetening agents, fragrances, and the like.

In accordance with a further aspect of the present invention, there is provided a method for preparing a functional food composition for treatment of allergy, comprising:

collecting, washing and drying herbal plant materials of *Poncirus trifoliata, Saururus chinensis, Schisandra chinensis,* and *Plantago asiatica,* respectively;

placing the dried herbal plant materials in 50 to 60-fold weight of water, a $C_2$-$C_6$ lower alcohol or a mixture thereof as an extraction solvent, followed by extraction at a temperature of 50 to 150° C. for 1 to 10 hours;

concentrating the hot water extracts or alcoholic extracts of the herbal plant materials at a temperature of 50 to 150° C. for 10 to 24 hours; and mixing the herbal plant concentrates in a ratio of 30 to 80% by weight of *Poncirus trifoliata* extract concentrate, 5 to 20% by weight of *Saururus chinensis* extract concentrate, 5 to 25% by weight of *Schisandra chinensis* extract concentrate, and 5 to 30% by weight of *Plantago asiatica* extract concentrate.

Preferably, the extraction solvent may be used in an amount of 50 to 60-fold weight relative to each herbal plant material.

In another embodiment of the present invention, the method comprises:

collecting, washing and drying herbal plant materials of *Poncirus trifoliata, Saururus chinensis, Schisandra chinensis,* and *Plantago asiatica,* respectively;

mixing the dried herbal plant materials in a ratio of 30 to 80% by weight of *Poncirus trifoliata,* 5 to 20% by weight of *Saururus chinensis,* 5 to 25% by weight of *Schisandra chinensis,* and 5 to 30% by weight of *Plantago asiatica,* and placing the mixture in 50 to 60-fold weight of water, a $C_2$-$C_6$ lower alcohol or a mixture thereof as an extraction solvent, based on the total weight of the herbal plant materials, followed by extraction at a temperature of 50 to 150° C. for 1 to 10 hours; and concentrating the hot water extracts or alcoholic extracts of the herbal plant materials at a temperature of 50 to 150° C. for 10 to 24 hours.

In accordance with yet another aspect of the present invention, there is provided a method for preparing a tea composition for treatment of allergy, comprising adding 80 to 90% by weight of purified water to 10 to 20% by weight of the aforesaid functional food composition.

The composition may further comprise one or more common food additives known in the art, such as sterilizers, fragrances, seasonings, vitamins, natural flavors, and the like.

Advantageous Effects

As will be described hereinafter, functional food and tea compositions for treatment of allergy in accordance with the present invention are therapeutically effective for any type of allergic diseases, irrespective of allergic causes. In particular, the tea composition advantageously enables easy and regular administration at need, which can achieve anti-allergic effects without particular efforts for treatment of diseases.

Hereinafter, the present invention will be described in more detail as the best mode to practice the invention.

The present invention is directed to a functional food composition for treatment of allergic diseases, comprising *Poncirus trifoliata* extract, *Saururus chinensis* extract, *Schisandra chinensis* extract, and *Plantago asiatica* extract, as active ingredients.

The trifoliate orange used as a raw material in the present invention is *Poncirus trifoliata,* and Ponciri Fructus is the dried immature fruit of *Poncirus trifoliata. Poncirus trifoliata* grows in Korea, China and Japan. The fruits are mostly semi-circular and 1-4 cm in diameter. *Poncirus trifoliata* is clinically used as a remedy for chest pain, abdominal pain and dyspepsia, so as to eliminate bloating sensation in the chest and abdomen. Recently in China, an injectable preparation of *Poncirus trifoliate* was developed and used to achieve rapid therapeutic effects on acute myocardial infarction. However, there is no case reporting that *Poncirus trifoliata* is used for the treatment of allergic diseases, as illustrated in the present invention. The fruit rind of *Poncirus trifoliata* has a brown or greenish brown color and a large number of coarse, hollowed and small spots, and the inside of the fruit has a dirty white or gray brown color and 8 to 16 small compartments being radially disposed and aligned from the center, wherein each compartment is dry and yellowish brown, is dented and often contains immature seeds. Further, it has a bitter taste and an acrid smell. *Poncirus trifoliata* contains various ingredients, for example essential oils, typically such as (+)-limonene, linalool and citral, flavonoids, contained mainly in the pericarp, such as hesperidin, neohesperidin, naringin and poncirin, and coumarins such as umbilliferone, auraptene, citroptene, imperatorin, isoimperatorin, and isoponcimarin. Further, other substances such as citric acid and synephrine are also found in the fruit of the plant.

*Saururus chinensis* is white in root, leaves and flowers, and has been used in oriental herbal medicine for a long time. For example, the herbal plant is dried and used to treat or ameliorate skin dropsy, dysuria with painful difficult urination, beriberi, jaundice and hepatitis. However, to the best of our knowledge, there is no case in which *Saururus chinensis* is used for treatment of allergic diseases, as shown in the present invention.

*Schisandra chinensis* bears deep red fruits with an egg shape or ball shape and a diameter of about 1 cm, which contains red juice and one or two reddish brown seeds. *Schisandra chinensis* has all the five tastes; sweet, sour, bitter, salty, and hot. And among them, sour taste is the strongest. There are 3 species of *Schisandra chinensis* in Korea, e.g. *Schizandra chinensis* Baill, *Schizandra nigra* Max., and *Kadsura japonica* Dunal. The *Schizandra chinensis* Baill is widely distributed on Taebaek mountain, one of Korea's Mountains. *Kadsura japonica* Dunal grows on islands in the south of Korea, whereas *Schizandra nigra* Max. grows on JeJu island. Further, *Schisandra chinensis* is widely distributed throughout Korea, Japan, Sakhalin island, and China. It contains shisandrins, gomisins, citral, malic, and citric acids that help strengthen the heart, reduce blood pressure, and improve the immune system. Therefore, it is used as an excellent tonic and restorative. *Schisandra chinensis* also helps improve lung function and acts as an expectorant reducing cough and thirst. *Schisandra chinensis* is usually taken as a drink by soaking the dried fruit in cold water with addition of honey or sugar, or otherwise in the form of a honeyed juice with fruits as a punch or a starch cake. Alternatively, it may also be taken as a tea or liquor which is made by boiling the *Schisandra chinensis* fruit with a chestnut, a jujube, rootlets of ginseng, or the like.

*Plantago asiatica* is the plant valuable in treating urological infections, including nephritis, cystitis and urethritis. For this purpose, the dried ripe seed of *Plantago asiatica* is soaked and the resulting sticky liquid is used as a herbal medicine. Prior to flowering, herb leaves are picked, dried and boiled, and then may be taken as tea to promote digestion and prevent gastric ulcers.

Herbal plant extract used in the functional food composition in accordance with one embodiment of the present invention may be separately prepared. Alternatively, the herbal plant extract may also be prepared in the form of a mixture of four herbal plant extracts by mixing *Poncirus trifoliata, Saururus chinensis, Schisandra chinensis* and *Plantago asiatica* in a ratio of 30-80% by weight: 5~20% by weight: 5~25% by weight: 5~30% by weight, and adding a 50 to 60-fold weight of water to the mixture, based on the total dry weight of the herbal plant materials, followed by extraction at a temperature of 50 to 150° C. for 1 to 10 hours.

EXAMPLES

Now, the present invention will be described in more detail with reference to the following Examples. These examples are provided only for illustrating the present invention and should not be construed as limiting the scope and spirit of the present invention.

Preparation of Tea Composition

Example 1

Preparation of Water Extracts of Herbal Plants 10 g of chopped *Saururus chinensis* (dried) herbal material was placed in 600 cc of purified water and stirred, followed by extraction at a temperature of about 90° C. for 10 hours to separate a filtrate. The resulting extract was concentrated under reduced pressure at 70° C. for 10 hours, and then freeze-dried at −30° C. to afford 3 to 5 g of a dried powder. According to the same procedure as above, 4 g of *Plantago asiatica* extract, 12 g of *Poncirus trifoliata* extract, and 6 g of *Schisandra chinensis* extract were obtained, except that 10 g of *Plantago asiatica*, 30 g of *Poncirus trifoliata*, and 15 g of *Schisandra chinensis* were used as herbal raw materials.

Example 2

Preparation of Water-Alcohol Extracts of Herbal Plants 5 g of *Saururus chinensis* dry powder, 5 g of *Plantago asiatica* dry powder, 10 g of *Poncirus trifoliata* dry powder, and 7 g of *Schisandra chinensis* dry powder were obtained in the same manner as in Example 1, except that 50% ethanol was used as a solvent.

Preparation of Functional Food Composition

Example 3

The herbal plant extract powders prepared in Example 1 were mixed in a ratio of 15% by weight: 15% by weight: 46% by weight: 24% by weight of *Saururus chinensis* extract powder, *Plantago asiatica* extract powder, *Poncirus trifoliata* extract powder and *Schisandra chinensis* extract powder to thereby prepare a functional food composition which is therapeutically effective for treatment of allergy.

Example 4

A functional food composition was prepared in the same manner as in Example 3, except that *Saururus chinensis*, *Plantago asiatica*, *Poncirus trifoliata* and *Schisandra chinensis* extract powders were mixed in a ratio of 20% by weight: 13% by weight: 53% by weight: 14% by weight.

Example 5

A functional food composition was prepared in the same manner as in Example 3, except that *Saururus chinensis*, *Plantago asiatica*, *Poncirus trifoliata* and *Schisandra chinensis* extract powders were mixed in a ratio of 13% by weight: 27% by weight: 40% by weight: 20% by weight

Example 6

A functional food composition was prepared in the same manner as in Example 3, except that *Saururus chinensis*, *Plantago asiatica*, *Poncirus trifoliata* and *Schisandra chinensis* extract powders were mixed in a ratio of 14% by weight: 14% by weight: 57% by weight: 15% by weight.

Experimental Example 1

Anti-Allergic Effects of Functional Food Compositions

An allergic skin prick test was carried to examine skin response to various antigens which may be responsible for the occurrence of allergy. For this purpose, clinical subjects were administered with a mixture of 30 g of each of functional food compositions obtained in Examples 3 to 6 with 200 mL of water, three times a day for 3 months. A drop of allergen solution (reagent for allergen detection: Histamine) was placed on the skin of the forearm or back of the subjects. A sterile lancet or needle was used to prick the skin reaching up o the epidermis, in order to make the standardized allergen solution soaked into the epidermis. Then, the intensity of skin reaction was measured and evaluated. The results thus obtained are given in Table 1 below.

TABLE 1

| Example No. | Swelling before administration | Swelling 10 days after administration | Swelling 30 days after administration | Swelling 60 days after administration | Swelling 90 days after administration |
|---|---|---|---|---|---|
| 3 | +++ | +++ | ++ | ++ | − |
| 4 | +++ | ++ | ++ | + | − |
| 5 | +++ | ++ | + | − | − |
| 6 | +++ | +++ | ++ | + | − |

※ −: No swelling (red spots, less than 1 mm in diameter)
+: Very slight swelling (red spots, less than 3 mm in diameter)
++: Swelling less than 3 mm in diameter, with formation of red spots
+++: Swelling with a diameter of 3 to 5 mm, in conjunction with formation of red spots
++++: Swelling having a larger diameter, in conjunction with formation of red spots, as compared to the scale "+++"

As can be seen from the results of Table 1, upon reviewing the results (average) of the allergic skin prick test after administration of the functional food composition of Example 3 to 40 subjects for 3 months, a diameter of skin swelling was reduced to less than 3 mm from Day 10 of administration to Day 30, and only slight skin swelling occurred 90 days after administration of the composition.

Administration of the functional food composition of Example 4 showed a reduction in a diameter of swelling after 10 days, appearance of slight swelling after 60 days, and no swelling after 90 days, thus confirming a rapid recovery from allergic diseases.

Administration of the functional food composition of Example 5 showed decreased swelling after 30 days, and insignificant formation of red spots with a diameter of less than 1 mm after 90 days.

Upon administration of the functional food composition of Example 6, there was also a reduction in a diameter of swelling even with formation of red spots after 10 days, slight swelling after 30 days, and no swelling lesions and red spots after 60 days.

Based on the results of Table 1 as above, it is believed that the functional food composition of Example 5 exhibits significant effects on improvement of allergic constitution of the patients, and combined administration of the functional food composition of Example 6 will further enhance the therapeutic effects. Preparation of Tea Composition Having Anti-Allergic Effects Example 7

Preparation of Tea Composition

A 10 to 20% by weight of a functional food composition is prepared as in Example 3, 0.01% by weight of vitamin B1, 0.5% by weight of citric acid, 5 to 10% by weight of sugar, and 75 to 84% by weight of purified water were mixed, and filtered in a centrifuge (7500 RPM/1.4 g). The mixture was sterilized in a high temperature instant sterilizer at 135° C. for 0.5 sec and filled in a retort which was then sterilized at 121° C. for 15 min, thereby preparing a tea beverage.

Comparative Example 1

A tea beverage was prepared in the same manner as in Example 7, except that a roasted rice powder was used instead of the herbal plant extract powder in accordance with the present invention.

Experimental Example 2

Anti-Allergic Effects Upon Oral Administration of Tea Composition

Tea compositions of Example 7 and Comparative Example 1 were administered ad libitum to patients with an allergic predisposition to house dust, mites, pollen, dandruff, or the like, twice a day for 3 months. Then, an allergic skin prick test was carried out in the same manner as in Experimental Example 1. The results thus obtained are given in Table 2 below.

As can be seen from the results of Table 2 as above, Comparative Example 1 exhibited no significant difference in anti-allergic effects before and after the administration of the tea composition, whereas Example 7 exhibited a significant decrease in allergic reaction 30 days after administration of the tea composition.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A functional food composition for treatment of one or more allergic manifestations selected from the group consisting of atopic dermatitis, urticaria, bronchial asthma, allergic rhinitis and allergic keratitis, comprising 30 to 80% by weight of *Poncirus trifoliata* extract, 5 to 20% by weight of *Saururus chinensis* extract, 5 to 25% by weight of *Schisandra chinensis* extract, and 5 to 30% by weight of *Plantago asiatica* extract.

2. The functional food composition according to claim 1, wherein the *Poncirus trifoliata, Saururus chinensis, Schisandra chinensis* and *Plantago asiatica* extracts are prepared by placing a raw material of each herbal medicinal plant in a 50 to 60-fold weight of purified water or an aqueous alcoholic solution, followed by extraction at a temperature of 50 to 150° C. for 1 to 10 hours.

3. The functional food composition according to claim 2, wherein the alcohol is a lower alcohol of 30 to 70%, 4. The functional food composition according to claim 2, wherein the composition is prepared by adding an excipient to a concentrate obtained by concentrating hot water extract or alcoholic extract of the herbal raw material at a temperature of 50 to 150° C. for 10 to 24 hours, as a main ingredient.

5. The functional food composition according to claim 4, wherein the composition is used as a powder which is obtained by freeze-drying of the herbal plant extract concentrate at a temperature of -10 to -40° C. for 3 to 20 hours.

6. A tea composition for treatment of one or more allergic manifestations selected from the group consisting of atopic dermatitis, urticaria, bronchial asthma, allergic rhinitis and allergic keratitis, comprising 10 to 20% by weight of the functional food composition of any one of claims 1 to 5 and 80 to 90% by weight of purified water.

7. A method for preparing a functional food composition for treatment of one or more allergic manifestations selected from the group consisting of atopic dermatitis, urticaria, bronchial asthma, allergic rhinitis and allergic keratitis, comprising:

TABLE 2

|  | Swelling before administration | Swelling 10 days after administration | Swelling 30 days after administration | Swelling 60 days after administration | Swelling 90 days after administration |
|---|---|---|---|---|---|
| Ex. 7 | +++ | +++ | ++ | + | − |
| Comp. Ex. 1 | +++ | +++ | +++ | +++ | ++ |

※ −: No swelling (red spots, less than 1 mm in diameter)
+: Very slight swelling (red spots, less than 3 mm in diameter)
++: Swelling less than 3 mm in diameter, with formation of red spots
+++: Swelling with a diameter of 3 to 5 mm, in conjunction with formation of red spots
++++: Swelling having a larger diameter, in conjunction with formation of red spots, as compared to the scale "+++"

collecting, washing and drying herbal plant materials of *Poncirus trifoliata*, *Saururus chinensis*, *Schisandra chinensis*, and *Plantago asiatica*, respectively;

placing the dried herbal plant materials in 50 to 60-fold weight of water, a $C_2$-$C_6$ lower alcohol or a mixture thereof as an extraction solvent, followed by extraction at a temperature of 50 to 150° C. for 1 to 10 hours;

concentrating the hot water extracts or alcoholic extracts of the herbal plant materials at a temperature of 50 to 150° C. for 10 to 24 hours; and mixing the herbal plant concentrates in a ratio of 30 to 80% by weight of *Poncirus trifoliata* extract concentrate, 5 to 20% by weight of *Saururus chinensis* extract concentrate, 5 to 25% by weight of *Schisandra chinensis* extract concentrate, and 5 to 30% by weight of *Plantago asiatica* extract concentrate.

8. A method for preparing a tea composition for treatment of one or more allergic manifestations selected from the group consisting of atopic dermatitis, urticaria, bronchial asthma, allergic rhinitis and allergic keratitis, comprising adding 80 to 90% by weight of purified water to 10 to 20% by weight of the functional food composition of any one of claims 1 to 5.

* * * * *